US005624664A

United States Patent [19]
Lambrechts

[11] Patent Number: 5,624,664
[45] Date of Patent: Apr. 29, 1997

[54] SKIN CONDITIONING COMPOSITION AND SOFTGEL FILLED THEREWITH

[76] Inventor: John Lambrechts, 20730 Dearborn St., Chatsworth, Calif. 91313-2157

[21] Appl. No.: 380,747

[22] Filed: Jan. 30, 1995

[51] Int. Cl.$^6$ .................................................. A61K 7/44
[52] U.S. Cl. ................................................................ 424/60
[58] Field of Search ................ 424/60, 70.1, 78.02, 424/78.03; 514/873, 844, 846, 847, 848, 860–865, 886, 887, 937, 962

[56] References Cited

U.S. PATENT DOCUMENTS

| | | | |
|---|---|---|---|
| 4,316,902 | 2/1982 | Yu et al. | 424/266 |
| 4,363,815 | 12/1982 | Yu et al. | 424/274 |
| 4,367,224 | 1/1983 | Van Scott et al. | 424/175 |
| 4,424,234 | 1/1984 | Alderson et al. | 424/317 |
| 5,124,313 | 6/1992 | Schaeffer et al. | 514/2 |
| 5,147,861 | 9/1992 | Della Valle et al. | 514/54 |
| 5,364,617 | 11/1994 | Bush et al. | 424/59 |
| 5,382,432 | 1/1995 | McCook et al. | 424/401 |
| 5,492,935 | 2/1996 | Yu et al. | 514/703 |

*Primary Examiner*—James J. Seidleck
*Assistant Examiner*—Michael A. Williamson
*Attorney, Agent, or Firm*—Jeffer, Mangels, Butler & Marmaro LLP

[57] ABSTRACT

A skin conditioning composition includes an acid or combination of acids selected from the group consisting of hydroxy acids and keto acids and is capable of being stably encapsulated within a gelatin shell.

18 Claims, No Drawings

SKIN CONDITIONING COMPOSITION AND SOFTGEL FILLED THEREWITH

FIELD OF THE INVENTION

The present invention relates to an improved skin conditioning formulation, more particularly a formulation containing an α-hydroxy, β-hydroxy or keto acid, that is suitable for use as a fill in a gelatin capsule.

BACKGROUND OF THE INVENTION

A soft, supple and flexible skin has a marked cosmetic appeal and is an attribute of normal functioning epidermis. As human skin ages with advancing years, the epidermis can become folded, ridged or furrowed to form wrinkles. These signal loss of youthful appearance and herald the transition to old age. Exposure to excessive doses of sunlight accelerates the transition process. The outer layer of the epidermis (the stratum corneum) can also become dry and flaky following exposure to cold weather or excessive contact with detergents or solvents. Loss of skin moisture thereby results, and the skin begins to lose the soft, supple and flexible characteristics.

Emollients such as fats, phospholipids and sterols have in the past been used to soften wrinkled or dry skin. These emollients have proven to be only partially effective in improving the condition of the skin.

Carboxylic acids have been employed successfully in improving the quality of human skin, by moisturizing the skin and exfoliating dead skin cells from the epidermal layer. In particular, α-hydroxy carboxylic acids ("α-hydroxy acids"), β-hydroxy carboxylic acids ("β-hydroxy acids") and carboxylic acids including an α or β keto group ("keto acids") have proven highly effective therapeutically. Compositions and methods employing α-hydroxy acids are disclosed in a large number of patents. U.S. Pat. No. 4,105,782, to Yu et al., discloses the use of amines or ammonium salts of α-hydroxy carboxylic acids in the treatment of acne or dandruff. U.S. Pat. Nos. 4,021,572, 4,105,783, 4,197,316 and 4,363,815, to Yu et al., teach the use of free α- and β-hydroxy acids and keto acids, and also peroxides, amides, lactones, anhydrides, esters, and salts of such acids, for the treatment of numerous skin conditions, including dry skin, ichthyosis, keratoses and hyperkeratoses, psoriasis, eczema, etc. U.S. Pat. No. 4,234,599, to Van Scott et al., reveal the use of α-hydroxy carboxylic acids, their esters or amine salts in the treatment of keratoses. U.S. Pat. No. 4,424,234, to Alderson et al., teaches skin treatment compositions incorporating α-hydroxycaproic acid and α-hydroxycaprylic acid or mixtures thereof in acidic compositions (pH typically from 2 to 4). U.S. Pat. No. 5,091,171, to Yu et al., describes the use of such compounds against age spots, wrinkles and aging related skin changes.

Although compositions including hydroxy and/or keto acids have proven very successful in treating many skin conditions, they are not without certain problems. For example, exposure of new or previously untreated skin to α-hydroxy acid compositions can cause irritation, particularly if the treatment is carried out too quickly. U.S. Pat. No. 5,382,432, to McCook et al., addressed this problem by using a series of compositions having increasing concentrations of α- or β-hydroxy acids over time, in order to allow the skin of the user to grow accustomed to the irritation produced by the acids.

The known skin conditioning compositions which include hydroxy or keto acids have typically been prepared in the form of lotions, sprays, creams, molded sticks, and the like, and have been packaged and dispensed from conventional tubes, lidded jars, aerosol or pump spray containers, stick applicators, etc. With the development of the soft gelatin capsule, or softgel, an alternative form of dispensing and applying such skin conditioning compositions has become available. Encapsulation of a skin conditioning composition in a softgel offers numerous advantages. For example, no additional packaging would be needed for the filled softgels. The compositions could be prepared in pre-measured quantities effective to moisturize the skin of the user, thus minimizing waste of the compositions.

For practicable encapsulation within a softgel, however, the skin conditioning composition must be compatible with the softgel. In particular, the composition must be formulated such that it can be stably encapsulated in the softgel shell without dissolving the softgel. The composition should be formulated such that it is stable in encapsulated form for extended periods of time at room temperature.

A need exists for skin conditioning compositions including hydroxy and/or keto acids that are compatible with a softgel shell and can be encapsulated stably in a softgel. Desirably, the compositions should be gentle to the skin as well.

SUMMARY OF THE PREFERRED EMBODIMENTS

In accordance with one aspect of the present invention, there is provided a skin conditioning composition including at least one hydroxy or keto acid which is capable of being stably encapsulated within a gelatin shell. Preferably, the inventive composition has an equilibrium relative humidity of less than about 65%.

In a preferred embodiment, the inventive composition includes at least one α-hydroxy acid, β-hydroxy acid or keto acid. Particularly preferably, the inventive composition includes an α-hydroxy acid such as lactic acid and/or glycolic acid.

Preferably, the skin conditioning composition is an emulsion. An acid solution comprising at least one hydroxy or keto acid forms the internal (dispersed) phase, and a thixotropic agent constitutes the external (continuous) phase. An emulsifying agent which is compatible with gelatin is also included in the inventive composition. Preferably, the acid is present in an amount effective to moisturize human skin.

According to another aspect of the present invention, a skin conditioning product includes a skin conditioning composition as described above, encapsulated in a gelatin shell.

According to a further aspect of the present invention, a method of moisturizing human skin includes the steps of dispensing a skin conditioning composition encapsulated in a skin conditioning product as described above from its gelatin shell, and applying the composition to the skin.

Other objects, features and advantages of the present invention will become apparent to those skilled in the art from the following detailed description. It is to be understood, however, that the detailed description and specific examples, while indicating preferred embodiments of the present invention, are given by way of illustration and not limitation. Many changes and modifications within the scope of the present invention may be made without departing from the spirit thereof, and the invention includes all such modifications.

DETAILED DESCRIPTION OF THE PREFERRED EMBODIMENTS

Applicant has discovered that skin conditioning compositions that include hydroxy acids and/or keto acids and that are useful in combination with soft gelatin shells can be prepared by limiting the amount of active, or "free", water in the composition. The low amount of free water in the inventive compositions ensures that the compositions do not adversely interact with soft gelatin shells, e.g., by migration of free water into the gelatin shells. In general, a composition according to the invention includes an excessive amount of free water if soft spots form in a gelatin shell within which the composition is encapsulated. More particularly, skin conditioning compositions according to the invention preferably have a very low equilibrium relative humidity (ERH). The ERH is a measure of the amount of water in a composition that is free, or "active." In most compositions containing water, at least a portion of the water molecules is strongly bound to various sites, in particular polar sites, on the various chemical constituents of the composition. Such sites include hydroxyl groups, carboxyl groups, carbonyl groups, amino groups, and other sites that are capable of binding water by hydrogen bonding, ionic bonding, etc. Additional quantities of water molecules may be bound less strongly, yet still be effectively unavailable as a solvent for the composition or for materials with which the composition comes into contact. The remaining water is unbound, that is, free.

The ERH of a composition is measured by determining the humidity, in an enclosed volume, at which the vapor pressure of water contained in the composition is equal to the vapor pressure of water in the volume of air above the composition. ERH, and the related quantity of water activity (obtained by dividing the measured ERH by 100), can readily be measured using instruments available commercially from, e.g., Rotronic Instrument Corp. (Huntington, N.Y.). Various methods for measuring ERH and water activity are described in R. Marsill, "Water Activity: Why It's Important and How to Measure It," *Food Product Design*, December 1993, pp. 36–41, which is incorporated herein by reference.

Compositions having an ERH of less than about 65%, more preferably between about 65% and 35%, have proven suitable for encapsulation according to the invention and are therefore preferred.

The low ERH of the inventive compositions, in addition to facilitating encapsulation in gelatin shells, also minimizes the ionization of the acids in the compositions. Rather, the acids are ionized by the moisture present on the user's skin, which allows the acids to begin to act as soon as the compositions are rubbed into the skin.

Furthermore, the low ERH of the inventive compositions reduces the risk bacterial contamination. The amount of free water in the inventive compositions in general is too low to support bacterial growth.

The inventive compositions preferably are emulsions. The emulsions include an acid solution which comprises a hydroxy acid, a keto acid, or combination of hydroxy and/or keto acids as the internal (dispersed) phase. A thixotropic agent, preferably a gel, constitutes the external (continuous) phase. A gelatin-compatible emulsifying agent having a low hydrophilic/lipophilic balance (HLB) is also included.

In a first preferred embodiment of an emulsion according to the invention, the acid is an α-hydroxy acid, that is, a carboxylic acid having a hydroxyl substituent on a carbon atom which is in the α-position with respect to a carboxyl group. Such acids can have more than one hydroxyl substituent and/or more than one carboxyl group. The α-hydroxy acid can be any such acid which is useful in improving the condition of human skin. Exemplary α-hydroxy acids include glycolic acid, lactic acid, citric acid, glucuronic acid, galacturonic acid, malic acid, mandelic acid, mucic acid and glyceric acid.

In a second preferred embodiment of an emulsion according to the invention, the acid is β-hydroxy acid, defined analogously to an α-hydroxy acid. Useful β-hydroxy acids include β-hydroxybutyric acid.

In a third preferred embodiment of an emulsion according to the invention, the acid is a keto acid, more specifically an α- or β-keto acid. Useful keto acids include pyruvic acid.

Additional useful hydroxy and keto acids are disclosed in U.S. Pat. Nos. 4,363,815; 4,234,599; 4,197,316; 4,105,783; 4,105,782; 4,021,572; 3,988,470; 3,984,566; 3,920,835; and 3,879,537, the disclosures of each of which are incorporated in their entireties herein by reference.

Particularly preferred α-hydroxy acids are lactic acid and glycolic acid. Combinations of lactic acid and glycolic acid have proven especially beneficial. Lactic acid is an effective moisturizer and enhances skin penetration. Glycolic acid penetrates the skin rapidly and is a highly effective exfoliant.

The acid or combination of acids is preferably present in the inventive composition in a therapeutically effective amount, that is, an amount sufficient to improve at least one quality of human skin such as moisture content, smoothness, etc. Preferably, the acid or combination of acids is present in an amount effective to moisturize human skin. Typically, an effective moisturizing amount is about 0.1 wt % to about 30 wt %, more preferably about 5 wt % to about 15 wt %, particularly about 7 wt % to about 8 wt %, based on the total weight of the composition. Compositions having lower acid percentages are particularly suitable for daily use.

The acid or combination of acids employed preferably contains a low amount of water, particularly a low amount of free water. Preferably, the acid or combination of acids is concentrated up to about 70% to 80% or more.

Emulsions prepared according to the instant invention also include a thixotropic agent as the continuous (external) phase. The thixotropic agent preferably includes a gel, more preferably a gel comprising hectorite, propylene carbonate and a compatible oil. Such thixotropic agents are gelatin-compatible and possess suitable flow characteristics for encapsulation in gelatin shells. Exemplary preferred gels include Bentone Gel VS-5 PC (commercially available from Rheox Inc.), which includes cyclic dimethyl polysiloxane (CAS No. 69430-24-6), a "cyclomethicone", as the oil, and Myglyol Gel type B (commercially available from Huls America, Inc.), which includes caprylic/capric triglyceride as the compatible oil. Other similar hydrophobic gels can be obtained commercially or can be readily formulated by those skilled in the art.

Preferably, one or more additional oils can be combined with the gel. The additional oil or combination of oils should be compatible with the other ingredients of the composition and with gelatin. For example, polysiloxane oils, in particular cyclomethicones, can be added to polysiloxane-based gels. Preferred cyclomethicones are provided in 1401 Fluid and 344 Fluid (commercially available from Dow Corning). Such combinations have the advantage of requiring reduced amounts of emulsifying agents to form emulsions. Other oils can be employed depending on composition of the gel.

The thixotropic agent (including the gel and optional additional oil or oils) preferably is present in an amount from about 50 wt % to about 90 wt %. Larger amounts of acid in general will require larger amounts of the thixotropic agent.

Emulsions prepared according to the present invention also include an emulsifying agent which is compatible with gelatin and which has a low hydrophilic/lipophilic balance (HLB). The HLB is a numeric rating system for the combined hydrophilic and lipophilic characteristics of an amphiphilic molecule that contains both hydrophilic and lipophilic moieties, and thus is a measure of the emulsifying efficiency of a surfactant. The HLB is related to the polarity of the molecule, the least hydrophilic surfactants having low HLB numbers, and increasing numbers corresponding to increasing hydrophilic character. For example, a non-ionic surfactant having a low HLB value (i.e., less than about 10) is considered oil-soluble and favors water-in-oil emulsions, while a surfactant having a high HLB value (i.e., greater than about 13) is associated with a water-soluble surfactant and favors oil-in-water emulsions.

The assignment of numerical values for HLB based upon chemical groupings in a molecule is given by A. W. Adamson in "Physical Chemistry of Surfactants," 2nd ed. (Interscience Publishers, New York 1967), pp. 520–522. Adamson also provides references to experimental methods for the determination of HLB numbers of amphiphilic molecules. A detailed definition of HLB is also provided by M. J. Schnick, Surfactants Science Series, Vol. 1, Nonionic Surfactants, Chapter 18 (M. Dekker Inc., New York 1967).

For use in the present invention, preferred emulsifying agents are those non-ionic surfactants that are compatible with gelatin and with the thixotropic agent, in particular with cyclomethicone gels, and has an HLB from about 1–10. Suitable emulsifying agents include long-chain (preferably $C_{16}$ or higher, e.g., $C_{16-24}$) fatty acid monoesters of polyhydric alcohols, e.g., glyceryl monostearate, glyceryl monopalmitate, glyceryl monoarachidate, glyceryl monobehenate, sorbitan monolaurate, sorbitan monostearate, sorbitan monooleate, and sorbitan trioleate.

Glyceryl monoesters of long-chain fatty acids are particularly preferred. Such emulsifying agents are solid at room temperature. When heated and combined with the other ingredients of the inventive composition, then cooled, these emulsifying agents afford a homogeneous composition in which the acid internal phase is microencapsulated by the emulsifying agent. Glyceryl monostearate is particularly preferred due to its ability to microencapsulate the acid internal phase. Glyceryl palmitate is also highly useful, but typically requires use of a somewhat larger amount of gel in the composition.

Skin conditioning compositions employing the preferred glyceryl emulsifiers described above can also be formulated to be very gentle to the skin, in particular to minimize the irritation to the skin which can be caused by excessively rapid exposure of new skin to hydroxy and/or keto acids. As the compositions are rubbed into the user's skin, the shear forces generated by the rubbing action cause the acids to be released from encapsulation by the emulsifier. Thus, the acids are released over time to condition the skin.

Other emulsifying agents which remain liquid at room temperature are also useful but are less preferred, and generally require the use of larger amounts of gel. Combinations of emulsifying agents can also be used if desired.

The emulsifying agent or combination of agents preferably is present in an amount from about 1–10 wt %. Care should be exercised in selecting the amount of the emulsifying agent or agents, as excessive amounts can promote the formation of micelles and thus adversely affect the delivery of the hydroxy acid to the skin.

Optionally, skin conditioning compositions according to the invention can include one or more additional cosmetically useful ingredients, preferably those that are hydrophobic and compatible with gelatin. Such ingredients include, for example, emollients, humectants, sunscreen agents, antiseptics, preservatives, anti-oxidants such as tocopherol (Vitamin E), etc. Examples of the foregoing additional ingredients are disclosed in U.S. Pat. No. 4,424,234, to Alderson et al., which is incorporated herein by reference. Emollients can be employed in amounts up to about 0.5 wt %. Other additives can be present in amounts up to about 20 wt %. Such added ingredients preferably include few or no free aldehyde groups, which can adversely affect gelatin by cross-linking it.

The inventive emulsions preferably have a viscosity at 30° C. between about 500 and 20,000 cps. The viscosity of the emulsions can be controlled by varying the proportions of acid and gel, with relatively larger amounts of acid affording generally lower viscosities.

Emulsions according to the invention can be produced in any conventional manner. A typical emulsion is produced as follows: a suitable gel is provided and is combined with one or more additional compatible oils to form the thixotropic agent. The selected acid or combination of acids is prepared, as is the selected emulsifying agent. Subsequently, the acid or acid combination and the emulsifying agent are combined. The thixotropic agent is heated, and the combined acid(s) and emulsifying agent(s) are then slowly added with stirring to form the emulsion. The emulsion is then cooled and packaged.

The inventive skin conditioning compositions can be packaged, if desired, in conventional packaging such as plastic bottles, tubes, etc. A user can thus dispense the inventive composition from a conventional bottle or tube and apply the composition to her skin.

The inventive compositions are particularly suitable for encapsulation in a soft gelatin shell, or softgel (a one-piece, hermetically sealed soft gelatin shell containing a liquid, a suspension, or a semi-solid). Thus, according to a preferred embodiment, a user can dispense the inventive composition from such an encapsulating gelatin shell and apply the composition as described above to her skin.

Softgels including the inventive skin conditioning compositions can be produced using any conventional manufacturing process. The most common modern manufacturing process involved in the preparation of softgels is a continuous method whereby two gelatin ribbons pass between twin rotating dies. As the ribbons meet, the liquid to be encapsulated is precisely injected between them. The capsule halves are sealed and ejected by the continuous rotation of the dies. See P. Tyle, Specialized Drug Delivery Systems, Marcel Dekker, Inc. (1990) for a general discussion of softgel manufacturing and production technology, in particular, Chapter 10 by Paul K. Wilkinson and Foo Song Hom.

Various gelatin shell masses may be prepared, depending on the fill properties, climatic conditions, and end use. Typically gelatin formulations include the same basic ingredients, namely, gelatin, a plasticizer such as glycerin, water, and optionally preservatives. The formulations of gelatins are well known to those of ordinary skill in the art.

The typical rotary die process, which requires a flowable liquid or fill, is readily adaptable to accommodate the skin conditioning compositions of the instant invention.

Shell formulations are discussed in Van Hostetler and J. Q. Bellard noted below as well as in "Advances in Softgel Formulation Technology", M. S. Patel, F. S. S. Morton and H. Seager, *Manufacturing Chemists*, July 1989; "Soft Elastic Gelatin Capsules: A Unique Dosage Form", William R. Ebert, *Pharmaceutical Technology*, October 1977; "Soft gelatin capsules: a solution to many tableting problems", H. Seager, *Pharmaceutical Technology*, September 1985; U.S.

Pat. No. 4,067,960 to Fadda; U.S. Pat. No. 4,198,391 to Grainger; U.S. Pat. No. 4,744,988 to Brox; and U.S. Pat. No. 4,780,316 to Brox. These references are incorporated herein in their entireties by reference.

After the rotary die process is used to thereby produce gelatin shells having a skin conditioning composition of the instant invention as fill therein, the resulting capsules are typically washed with an evaporatable solvent. Thereafter, the capsules are typically tumble dried in a series of hollow drums with perforated walls. Room air (25° C.) is continuously pumped through the rotating drums. By the time the capsules exit this process, all of the solvent used in washing has typically been evaporated, and a large proportion (50–60%) of the water from the gelatin shell has been removed. Recent developments in drying include bypassing the drum drying stage and having the capsules dried in a drying tunnel or room as discussed below.

After the capsules exit the last drying drum, the capsules are typically spread on drying trays. The final drying phase for softgels is typically accomplished by passing the drying trays through drying tunnels or into drying rooms. Stacks of trays are inserted into drying tunnels or drying rooms, in which controlled temperature air (21°–24° C.) and low relative humidity (20–30%) is continuously circulated. Although additional water may be removed from dry capsules by further heating, for example at 40° C., such a procedure has not been found to be practical or necessary. See Van Hostetler and J. Q. Bellard in *The Theory and Practice of Industrial Pharmacy*, "Capsules", (1970), Chapter 13 at pages 346–383, and in particular at page 380.

The drying time, for most softgels, is 16–24 hours, but may be slightly longer if the softgels are over 20 minims in size or if the softgels contain a non-oily type liquid base. The Karl Fischer test is used for determining water content. The drying occurs typically at about 21°–24° C. and at a relative humidity of 20–40%.

Softgels permitted to come to water equilibrium in this controlled environment are considered "dry". After drying, the capsules are typically inspected and finished using varied known techniques.

A typical gelatin shell formulation includes 47 wt % gelatin, 15 wt % glycerin (USP), and 38 wt % water, optionally with additional colorant materials. Other shell formulations can readily be prepared by one of ordinary skill in the art.

Softgels having the inventive skin conditioning compositions as fill are capable of being stored for extended periods of time, typically up to 24–36 months or longer, at room temperature (25° C.).

The invention is further illustrated by reference to the following non-limiting examples.

EXAMPLE 1

An emulsion is prepared from the following ingredients:

| Ingredient | Amount (wt %) |
| --- | --- |
| Fluid 344* | 58.0 |
| Bentone Gel VS-5 PC | 30.0 |
| Lactic acid (88% solution) | 5.0 |
| Glycolic acid (70% solution) | 2.0 |
| Glyceryl monostearate | 5.0 |

*A polydimethylcyclosiloxane primarily comprising octamethylcyclotetrasiloxane, available from Dow Corning.

The external phase of the emulsion is prepared by adding Fluid 344 to the Bentone Gel VS-5 PC and mixing the two ingredients at 25° C. Next, the internal phase of the emulsion is prepared by combining the lactic and glycolic acids and heating the mixture to 65° C. The glyceryl monostearate is heated to melting and added to the acid mixture. The external phase is subsequently heated to about 55–60° C., and the internal phase is slowly added with stirring. The emulsion is then cooled to room temperature and encapsulated.

EXAMPLE 2

An emulsion is prepared from the following ingredients in the same manner as Example 1.

| Ingredient | Amount (wt %) |
| --- | --- |
| Fluid 1401** | 20.0 |
| Fluid 344 | 29.0 |
| Bentone Gel VS-5 PC | 33.0 |
| Lactic acid (88% solution) | 5.0 |
| Glycolic acid (70% solution) | 5.0 |
| Glyceryl monostearate | 8.0 |

**A mixture of cyclomethicone and dimethiconol, available from Dow Corning.

EXAMPLE 3

An emulsion is prepared from the following ingredients in the same manner as Example 1:

| Ingredient | Amount (wt %) |
| --- | --- |
| Fluid 344* | 58.0 |
| Myglyol Gel type B | 30.0 |
| Lactic acid (88% solution) | 5.0 |
| Glycolic acid (70% solution) | 2.0 |
| Glyceryl monostearate | 5.0 |

*A polydimethylcyclosiloxane primarily comprising octamethylcyclotetrasiloxane, available from Dow Corning.

The inventive skin conditioning compositions are highly effective in holding and depositing hydroxy and/or keto acids on and in the stratum corneum and epidermis of the user. The inventive compositions are useful to clean and prepare the skin for exfoliation by loosening dead skin cells and preparing new cells to grow and divide. The inventive compositions can also be targeted directly to areas of the skin which are in particular need of conditioning.

What is claimed is:

1. A skin conditioning product comprising a skin conditioning composition stably encapsulated in a gelatin shell, and skin conditioning composition comprising an acid or combination of acids selected from the group consisting of hydroxy acids and keto acids, wherein said composition is capable of being stably encapsulated within a gelatin shell and has an equilibrium relative humidity of less than about 65%.

2. The product of claim 1 wherein said hydroxy acid is an α-hydroxy acid.

3. The product of claim 2 wherein said α-hydroxy acid is selected from the group consisting of glycolic acid, lactic acid, citric acid, glucuronic acid, galacturonic acid, malic acid, mandelic acid, mucic acid and glyceric acid.

4. The product of claim 3 wherein said α-hydroxy acid is lactic acid or glycolic acid.

5. The product of claim 1 wherein said hydroxy acid is α-hydroxy acid.

6. The product of claim 1 wherein said keto acid is an α-keto acid or β-keto acid.

7. The product of claim 1 wherein said acid or combination of acids is present in an amount effective to moisturize human skin.

8. The product of claim 7 wherein said acid or combination of acids is present in an amount from about 0.5 wt % to about 15 wt % based on the total weight of the composition.

9. The product of claim 1 wherein said composition comprises a hydroxy acid or combination of hydroxy acids, a thixotropic agent and an emulsifying agent which is compatible with gelatin.

10. The product composition of claim 9 wherein said hydroxy acid is an α-hydroxy acid or a β-hydroxy acid.

11. The product composition of claim 9 wherein said thixotropic agent comprises a hydrophobic gel and a compatible oil.

12. The product composition of claim 9 wherein said emulsifying agent is compatible with said thixotropic agent and has an HLB from about 1–10.

13. The product composition of claim 12 wherein said emulsifying agent is a fatty acid monoester of a polyhydric alcohol.

14. The product composition of claim 13 wherein said emulsifying agent is selected from the group consisting of glyceryl monostearate, glyceryl monopalmitate and glyceryl monoarachidate and glyceryl monobehenate.

15. The product composition of claim 14 wherein said emulsifying agent is glyceryl monostearate.

16. The product composition of claim 9 further comprising an additive selected from the group consisting of emollients, humectants, sunscreen agents, antiseptics, preservatives and anti-oxidants.

17. The product composition of claim 9 wherein said composition comprises (a) about 50 wt % to about 90 wt % of a thixotropic agent;

(b) about 0.1 wt % to about 30 wt % of an acid or combination of acids selected from the group consisting of hydroxy acids and keto acids; and (c) about 1 wt % to 10 wt % of an emulsifying agent.

18. A method of improving the condition of human skin comprising the steps of dispensing the composition encapsulated in the skin conditioning product of claim 1 from said gelatin shell and applying said composition to said skin.

* * * * *